United States Patent
Allegretti et al.

(10) Patent No.: US 7,217,707 B2
(45) Date of Patent: May 15, 2007

(54) AMIDE OF R-2-(AMINOARYL)-PROPIONIC ACID FOR USE IN THE PREVENTION OF LEUCOCYTE ACTIVATION

(75) Inventors: Marcello Allegretti, L'Aquila (IT); Riccardo Bertini, L'Aquila (IT); Cinzia Bizzarri, L'Aquila (IT); Vilma Sabbatini, L'Aquila (IT); Ginfranco Caselli, Milan (IT); Maria Candida Cesta, L'Aquila (IT); Carmelo Gandolfi, deceased, late of Milan (IT); by Janete Peloia Barroso Gandolfi, legal representative, Milan (IT); by Giulio Agostino Gandolfi, legal representative, Milan (IT); by Maria Carla Gandolfi, legal representative, Milan (IT); by Arrigo Aldo Gandolfi, legal representative, Saronno (VA) (IT); Francesco Colotta, L'Aquila (IT)

(73) Assignee: Dompe S.p.A., L'Aquila (IT)

( * ) Notice: Subject to any disclaimer, the term of this patent is extended or adjusted under 35 U.S.C. 154(b) by 164 days.

(21) Appl. No.: 10/258,959

(22) PCT Filed: Apr. 11, 2001

(86) PCT No.: PCT/EP01/04137

§ 371 (c)(1),
(2), (4) Date: Oct. 30, 2003

(87) PCT Pub. No.: WO01/79189

PCT Pub. Date: Oct. 25, 2001

(65) Prior Publication Data

US 2004/0186146 A1    Sep. 23, 2004

(30) Foreign Application Priority Data

Apr. 14, 2000 (IT) .......................... MI2000A0836

(51) Int. Cl.
*A61K 31/54* (2006.01)
*C07D 211/00* (2006.01)

(52) U.S. Cl. ............................... 514/227.8; 514/235.5; 514/427; 544/60; 544/133; 546/246; 546/268.1; 548/561; 548/566

(58) Field of Classification Search .................. 544/60, 544/133; 546/246, 268.1; 548/561, 566; 514/227.8, 235.5, 427, 428
See application file for complete search history.

(56) References Cited

U.S. PATENT DOCUMENTS 3,669,956 A * 6/1972 Borck et al. ................ 540/611

OTHER PUBLICATIONS

Endo et al., Tetrahedron Letters, 1997, 58(12): 2113-2116.*
Singhvi et al., 1997, CAS: 127:140326.*
Hicks et al., 1979, CAS:91:204211.*
Ostermayer et al., 1971, CAS: 75:48900.*
Borck et al., 1970, CAS:73:25138.*

* cited by examiner

*Primary Examiner*—Joseph K. McKane
*Assistant Examiner*—Rei-tsang Shiao
(74) *Attorney, Agent, or Firm*—Birch, Stewart, Kolasch & Birch, LLP

(57) ABSTRACT

N-(2-aminoaryl-propionyl)-amides of formula (1) are described.

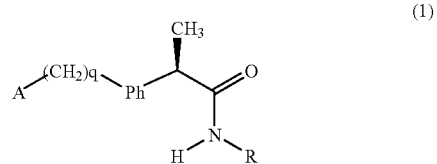

The process for their preparation and pharmaceutical preparations thereof are also described.

The amides of the invention are useful in the prevention and treatment of tissue damage due to the exacerbate recruitment of polymorphonuclear neutrophils (leukocytes PMN) at the inflammatory sites. In particular, the invention relates to the R enantiomers of 2-(aminoaryl)-propionyl amides of formula (1) for use in the ihibition of the chemotaxis of neutrophils induced by IL-8. The compounds of the invention are used in the treatment of psoriasis, ulcerative cholitis, glomerular nephritis, acute respiratory insufficiency, idiopathic fibrosis, and rheumatoid arthritis.

14 Claims, No Drawings

AMIDE OF R-2-(AMINOARYL)-PROPIONIC ACID FOR USE IN THE PREVENTION OF LEUCOCYTE ACTIVATION

This application is a 371 of PCT/EP01/04137 filed on Apr. 11, 2001.

TECHNICAL FIELD

The present invention relates to amides of R-2-aminoaryl-propionic acids and pharmaceutical compositions containing them, which are useful in the prevention and inhibition of leucocyte recruitment and activation and in the treatment of the pathologies strictly dependent on said activation.

BACKGROUND ART

Many physiological processes require that cells be in close contact with other cell populations and/or the extra-cellular matrices. These processes of adhesion are however necessary for activation, migration, proliferation and cell differentiation. Several families of cellular adhesion molecules (CAMs) that play an essential role in normal and patho-physiological processes mediate cell-cell-matrix interactions.

The process of cellular adhesion, essential for activation of neutrophils, is accompanied by the release of cytokines, among which are IL-8 and MCP-1 which allow amplification of the inflammatory process (see: Huang CD et al, Chang Keng J Hsueh, 22, 392, 1999; and B. Walzog et al, FASEB J., 13, 1855 1999).

The chemokines, in their turn, are distinguished, functionally, from other cytokines by the cellular specificity of their action: each of them regulates the migration and the function of a single cellular species in a specific way. Thus, while MCP-1 influences and directs the movements of monocytes, IL-8 carries out the pre-eminent role of neutrophil chemo-attracting factor.

This is confirmed by the presence of high concentrations of IL-8 in the sites of inflammation and in the surrounding fluid, measured in the course of many acute pathologies mediated by neutrophils, the prevention of serious tissue damage and the reduced infiltration by neutrophils observed after administration of IL-8 antibodies in the course of experiments on animal models showing neutrophil-dependent pathologies (see: Yang X D et al, J. Leukoc. Biol 66, 401, 1999). Typical clinical situations where neutrophil activation plays a prevailingly pathological role are damage resulting from cerebral reperfusion (Stanimirovic D and Satoh K, Brain Pathol., 10, 113 2000) and from ischemia and reperfusion of the myocardium.

These observations have confirmed the hypothesis that IL-8 constitutes the main mediator of neutrophil induced tissue damage to such an extent as to propose interleukin-8 as the optimal target for therapeutic intervention in neutrophil-dependent pathologies (N. Mukaida et al, Inflammation Res. 47 (Suppl. 3) S151, 1998). For this reason, as an alternative to the use of anti-IL-8 antibodies, low-molecular weight substances could be of great clinical interest and usefulness, said substances being able to insert into the inter- and intra-cellular signal transmission circuits, and to inhibit the migration of human neutrophils stimulated by IL-8 and similar substances (GRO-α, β, γ; ENA-78, NAP-2, GCP-2).

This is more current now that the determining role that the activation of certain kinases and tyrosine-kinases play in the dynamics of the IL-8 dependent chemotaxis event is becoming clearer.

For a long time it was suspected that the activation of certain tyrosine-kinases was the trigger event of the chemotaxis phenomenon after Yasui et al (J. Immunol. 152, 5922, 1994) demonstrated that complete inhibition of the PMN chemotaxis followed the inhibition of the activity of these enzymes.

More recently, the dramatic reduction of PMN chemotaxis, induced by a variety of chemokinic factors, observed in genetically modified rats deficient in the enzyme phosphoinositide 3-kinase (IP3K, Hirsch et al, Science, 287, 1049, 2000; Sasaki et al, Science, 287, 1040 2000), allows this enzyme to be characterized as the leader-kinase—primus movens of the successive cascade of events—and strengthens the belief in the specific and determining role carried out by the enzymatic processes of phosphorylation.

In the chemotaxis phenomena induced by interleukin-8 on PMN, besides phosphoinositide 3 kinase, an equally important role seems to be played by PyK2 (proline-rich tyrosine kinase) whose activation is essential for the development of the concomitant processes of cellular adhesion. In its turn, the process of activation of Pyk2, induced by IL-8 in PMN, is an IP3K dependent process that seems to happen and be localized in the areas of the cellular membrane dedicated to focal adhesion (Clark et al Science, 268, 233, 1995: Avraham et al, Blood, 88, 417, 1996), in direct contact with the cytoskeleton proteins involved in the adhesion phenomenon (e.g. vinculine, α-actine etc).

Also in the light of recent discoveries, it is believed that the therapeutic potential of new low-molecular weight molecules called to interfere with IL-8 dependent chemotaxis phenomenology is increased by some inhibitory activity towards the factors that promote adhesion and/or antagonist activity towards some integrines such as very late antigen 4 (VLA-4), LPAM-1, to block their linking to their ligands in order to usefully prevent ab initio the start of that cascade of events which, starting from the of intra-cellular adhesion processes, translate into neutrophil activation.

Recently N-acylsulfonamides and R-2-arylpropionic acid amides have been described (WO 00/24710 and PCT/EP01/01285, respectively), that are characterized by the selectivity of their inhibitory activity of IL-8-stimulated chemotaxis of human neutrophils. In the course of studies directed to define their molecular mechanisms of action, it was observed that they show a very substantial (70%–80% of inhibition), dose-dependent, inhibitory activity towards Pyk2-tyrosine-kinase activity for concentrations ranging from $10^{-7}$ to $10^{-8}$ M not dissimilar from the concentrations which show an effective inhibition of IL-8 dependent chemotaxis.

Furthermore, the activity of said amides and N-acylsulfonamides of R-2-arylpropionic acids seems to be totally independent from their involvement in the inhibition of (COX-1 and/or COX-2) cyclooxygenase dependent inflammatory processes.

There is also accumulated evidence that the inhibition of prostaglandin (PG) synthesis by (S)-enantiomers of 2-arylpropionic acids and certain 2-aryl-acetic acids can, in the long term, negatively reflect on the dynamics of the neutrophil-dependent inflammatory process, where inhibition of PG synthesis, and therefore of PGE2 removes a control factor of the endogenous synthesis of TNF-α. Accordingly, in competition with the same IL-8, TNF-α may contribute, with IL-6 and IL-1 cytokines and with the adhesion molecules (E-selectine, ICAM-1 and C-reactive protein) to worsen the entity and severity of tissue damage in the course of acute myocardium infarct (R. Pudil et al, Clin Chim Acta, 280, 127, 1999).

DISCLOSURE OF THE INVENTION

It has now been found that amides of (R)-2-phenylpropionic acids bearing a nitrogen containing substituents on the phenyl group, have surprising inhibition properties of IL-8 induced chemotaxis. Examples of such substituents are alkylamino or dialkylamino groups and nitrogen containing heterocycles. The compounds of the invention show enhanced water solubility and optimized pharmacokinetic characteristics with respect to other amides such as those described in PCT/EP01/01285.

The stereochemistry, the electronic, polar and steric effects of substituents on the amide nitrogen contribute to modulating the inhibition property of the IL-8 induced chemotaxis.

DETAILED DESCRIPTION OF THE INVENTION

The following paragraphs provide definitions of outstanding chemical moieties that make up the compounds according to the invention and are intended to apply uniformly throughout the specification and claims unless an otherwise expressly set out definition provides a broader definition.

"$C_1$–$C_3$-alkyl" or "$C_1$–$C_5$-alkyl" refer to monovalent alkyl groups having 1 to 3 or 1 to 5 carbon atoms. These terms are exemplified by groups such as methyl, ethyl, n-propyl, isopropyl, n-butyl, isobutyl, tert-butyl, and the like.

"$C_3$–$C_7$-cycloalkyl" refers to cycloalkyl groups having 3 to 7 carbon atoms. These terms are exemplified by groups such as cyclopropyl, cyclobutyl, cyclopentyl, cyclohexyl, and the like. Examples of $C_3$–$C_7$-cycloalkyl-$C_1$–$C_3$-alkyl groups are cyclopropyl methyl or cyclopentyl methyl.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, biphenyl, naphthyl, phenantrenyl and the like.

"Substituted or unsubstituted": unless otherwise constrained by the definition of the individual substituent, the above set out groups, like "alkyl", "cycloalkyl", "aryl" groups etc. can optionally be substituted with from 1 to 5 substituents selected from the group consisting of "$C_1$–$C_3$-alkyl", "$C_1$–$C_3$-alkyl aryl", "$C_1$–$C_3$-alkyl heteroaryl", primary, secondary or tertiary amino groups or quaternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides or cycloalkanes, but also acetals, thioacetals, aminals formed by ring closure for instance in an effort to obtain a protective group.

"Pharmaceutically acceptable salts" refers to salts or complexes of the below-identified compounds of formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art. Examples of salts also include organic bases such as tromethamine, L-lysine, L-arginine and the like.

The present invention relates to amides of the (R)-enantiomers of 2-arylpropionic acids, of formula (1):

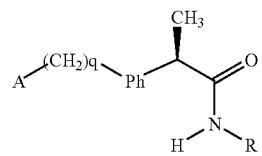

(1)

and pharmaceutically acceptable salts thereof,
wherein:
q is zero or the integer 1;
Ph represents a phenylene group linked to the group —(CH$_2$)$_q$-A in its position 2, 3 or 4 and optionally substituted in the remaining positions by one or more substituents, same or different, chosen from $C_1$–$C_3$-alkyl, halogens, $C_1$–$C_3$-alkoxy, hydroxy, SH, $C_1$–$C_3$-alkylthio, nitro, haloalkyl.

A is:
a N—$C_1$–$C_5$-alkylamino group, a N,N—$C_1$–$C_5$-dialkylamino group, a N—$C_1$–$C_8$-alkanoyl(cycloalkanoyl, arylalkanoyl)-N—$C_1$–$C_5$-alkylamino group;
a saturated or unsaturated nitrogen containing 5–7 membered heterocyclic ring;
a residue of formula (2a):

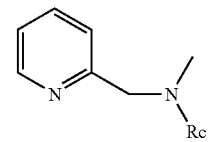

(2a)

wherein R$_c$ is hydrogen, $C_1$–$C_3$-alkyl or the residue of a $C_1$–$C_3$-alkanoic acid;
R is:
H; —SO$_2$—CH$_3$; $C_1$–$C_3$-alkyl, a residue of formula —CH$_2$—CH$_2$—X—(CH$_2$—CH$_2$O)$_n$—P where P is H, methyl, ethyl, isopropyl; —CH$_2$CO$_2$R$_1$, wherein R$_1$ is H or $C_1$–$C_3$; n is an integer from 0 to 5, X is O or S;
a residue of formula (3)

—(CH$_2$)m-Φ    (3)

wherein, when m is an integer from 2 to 3, Φ represents an unsubstituted or substituted phenylene as defined above, 2-(1-methyl-pyrrolidyl), 2-pyridyl, 4-pyridyl, 1-imidazolyl, 4-imidazolyl, 1-methyl-4-imidazolyl, 1-methyl-5-imidazolyl, or a group —NRa,Rb wherein each of Ra and Rb, same or different, represents $C_1$–$C_5$-alkyl or hydroxyalkyl-(CH$_2$)$_{mi}$—OH wherein m$_i$; is an integer from 2 to 3, or Ra and Rb, together with the N atom to which they are bound, constitute a heterocyclic ring of from 3 to 7 members; when m is zero, Φ is selected from the group of 2- or 4-pyridyl, 2- or 4-pyrimidinyl, 2-pyrazinyl, 5-methyl-2-pyrazinyl, 1-1,2,4-thiadiazolyl, 3-1,2,4-triazolyl, 3-1-benzyl-1,2,4- triazolyl, 2-1,3-thiazolidinyl, 2-1,3-thiazolyl, 3-isoxazolyl, dihydro-isoxazol-4-yl, 5-methyl-isoxazol-4-yl, 2-imidazolyl, imidazol-4-yl-5-carboxyamide, imidazol-2-yl-4,5-dicarbonitrile, 5-indanyl, 5-indazolyl, 7-aza-indol-3-yl, indol-3-yl, 2- or 3- or 4-quinolyl;

a residue of an α-amino acid selected from the group of alanine, valine, leucine, isoleucine, nor-leucine, phenylalanine, p-fluoro-phenylalanine, tyrosine, biphenylalanine, 2'-methoxy-biphenylalanine, tryptophan, 7-azatryptophan, histidine, S-methylcysteine, carboxymethylcysteine, methionine, O-methyl-serine, O-ethyl-serine, glycine, phenyl- or p-fluorophenyl-glycine;

a residue of an acid chosen from the group of β-alanine, γ-aminobutyric, δ-aminovaleric, cis-4-amino-cyclohexanecarboxylic, trans-4-amino-methyl-cyclohexanecarboxylic and 3-amino-1,5-pentadioic acid;

a residue of formula (3a)

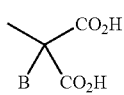

(3a)

wherein B represents H; a straight or branched $C_1$–$C_5$-alkyl; $(CH_2)_{ni}$—$NH_2$; —$(CH_2)_{ni}$—NH-t-butoxycarbonyl; —$(CH_2)_{ni}$—NH-benzyloxycarbonyl; —$(CH_2)_{ni}$—$CO_2H$ wherein $n_i$ is an integer between 1 and 3; benzyl; p-fluorobenzyl; p-phenyl-benzyl; p-(2-methoxy-phenyl)-benzyl; —$CH_2O$—$C_2H_5$; —$CH_2$—S—$CH_3$; —$CH_2$—S—$CH_2$—$CO_2H$; indolyl-3-methyl; 7-aza-indolyl-3-methyl;

provided that when q is zero, R is $SO_2CH_3$ and Ph is 3-chloro-1,4-phenylene, A is other than 1-2,5-dihydro-pyrrolidino.

The latter compound, wherein A is 1-2,5-dihydro-pyrrolidino, is described in WO 00/24710.

The salts of compounds of formula (1) with pharmaceutically acceptable bases and acids are a further object of the present invention.

Ph is preferably linked to the (—$CH_2$)q-A group in position 3 or, more preferably, in position 4. Ph is more preferably 1,4-phenylene unsubstituted or substituted in 3, for example by a chlorine.

A is preferably N,N-dimethylamino, N,N-diethylamino, N-methyl-N-ethyl-amino, N-acetyl-N-methyl-amino, N-pivaloyl-N-ethyl-amino or a nitrogen containing ring selected from 1-pyrrolidine, 1-2.5-dihydro-pyrrolidine (or 1-3-pyrroline), 1-pyrrol, 1-piperidino, 1-piperazino-4-unsubstituted or 4-substituted (methyl, ethyl, 2-hydroxyethyl, benzyl, benzhydryl or phenyl)-4-morpholine, 4-3,5-dimethyl-morpholine, 4-thiomorpholine.

Examples of 3 to 7 member heterocyclic rings formed by the —$NR_aR_b$ group comprise 4-morpholino, 1-piperidino, 1-piperazino and 4-substituted-1-piperazine (4-methyl, 4-benzyl, 4-2-phenylethyl).

Examples of compounds according to the invention are:

R—N-2-[4-(pyrrolidine-1'-yl)methylphenyl]propionyl-methansulfonamide;
R—N-2-[4-(4'-benzyl-piperazin-1'-yl-aminomethyl)-phenyl]-propionyl-methansulfonamide;
(R,S')-2-[3'-chloro-4-(thiomorpholin-4-yl)phenyl]-N-(2-carboxyethyl)propionamide;
(R)-2-[(3-chloro-4-(thiomorpholin-4-yl)phenyl]-N-(2-methoxycarbonylmethyl)propionamide;
(R,S')-2-[(3-chloro-4-(thiomorpholin-4-yl)phenyl]-N-[1(3,5-dimethyl-benzyl-oxycarbonyl)-ethyl-2-(3-indolyl)]-propionamide;
(R,S')-2-[(3-chloro-4-(thiomorpholin-4-yl)phenyl]-N-[1-(benzyloxycarbonyl)ethyl-2-(4'-fluorophenyl)]-propionamide;
R-2-[3-chloro-4-(3-pyrrolin-1-yl)-phenyl]-propionamide;
(R)-2-[3-chloro-4-(2,5-dihydro-1H-pyrrol-1)phenyl]-N—(N',N'-dimethyl-aminopropyl)-propionamide;
(R)-2-[3-chloro-4-(2,5-dihydro-1H-pyrrol-1)phenyl]-N-(bis-carboxymethyl)propionamide;
R(–)-2-[3-chloro-4-(piperidin-1-yl)phenyl]-N-(2''-hydroxyethoxy-ethyl)propionamide;
(R)-2-(4-morpholinophenyl)-N-(4'-pyrimidinyl)-propionamide;
R-2-[4-((N-ethyl-N-quinol-2'-yl-methyl-amino)-methyl)phenyl]-N-(2'-allyloxy-carbonyl-methyl)-propionamide;
(R,R')-2-[3-chloro-4-(piperidin-1-yl)]-N-[1'-methyl-2'-(2''-hydroxyethoxy)ethyl]-propionamide;
(R)-2-(4-morpholinophenyl)-N-(4'-pyrimidinyl)-propionamide;
(R)-2-[4-((N-ethyl-N-quinol-2-yl-methylamino)methyl)phenyl)]-N-(4'-pyridyl)-propionamide;
R-2-[3-chloro-4-(pyrrolidin-1-yl)-phenyl)]-N-(2'-pyridyl)-propionamide;
R-2-[3-chloro-4-(3-pyrrolin-1-yl)-phenyl]-N-(4'-pyridyl)-propionanimide;
R-2-[3-cloro-4-(1H-pyrrol-1-yl)-phenyl]-N-(4'-pyridyl)-propionamide;
R-2-[3-chloro-4-(morpholin-4-yl)-phenyl]-N-(1,3-tiazol-2-yl)-propionamide;
R-2-[4-(morpholin-4-yl-aminomethyl)-phenyl]-N-(pirazin-2-yl)-propionamide;
R-2-[3-chloro-4-(3'-pyrrolin-1-yl)-phenyl]-N-(4'-pyrimidinyl)-propionammide;
R-2-[4-(pyrrolidine-1-yl-methyl)-phenyl]]-N-(4'-pyridyl)-propionamide;
R-2-[4-(3-pyrrolin-1-yl)-phenyl]-N-(4'-pyridylethyl)-propionamide;
R-2-(4-piperidin-1-yl-phenyl)-N-(1-imidazol-ethyl)-propionamide;
R-2-[3-chloro-4-(pyrrolidin-1-yl)-phenyl)]-N-(2'-pyridyl)-propionamide;
R-2-[3-chloro-4-(3-pyrrolin-1-yl)-phenyl]-N-(4'-pyridyl)-propionamide;
R-2-[3-chloro-4-(1H-pyrrol-1-yl)-phenyl]-N-(4'-pyridyl)-propionamide;
R-2-[3-chloro-4-(morpholin-4-yl)-phenyl]-N-(1,3-thiazol-2-yl)-propionamide;
R-2-[4-(morpholin-4-yl-aminomethyl)-phenyl]-N-(pyrazin-2-yl)-propionamide;
R-2-[3-chloro-4-(3'-pyrrolin-1-yl)-phenyl]-N-(4'-pyrimidinyl)-propionamide;
R-2-[4-(pyrrolidin-1-yl-methyl)-phenyl]]-N-(4'-pyridyl)-propionamide;
R-2-[4-(3-pyrrolin-1-yl)-phenyl]-N-(4'-pyridylethyl)-propionamide;
R-2-(4-piperidin-1-yl-phenyl)-N-(1-imidazol-ethyl)-propionamide;
(R)-2-[4-(2,5-dihydro-1H-pyrrol-1-yl-methyl)phenyl]-propionyl-methansulfonamide;
(R)-2-[4-(2,5-dihydro-1H-pyrrol-1-yl-methyl)phenyl]-N-(2-carboxyethyl)-propionamide;
(R)-2-[4-(2,5-dihydro-1H-pyrrol-1-yl-methyl)phenyl]-propionamide.

Particularly preferred are compounds of formula (1) wherein the phenylene group Ph is a non-substituted 1-4 phenylene or C-3 monosubstituted or C-3,C-5 disubstituted phenylene.

Preferred are also compounds of formula (1) wherein R is an amino acid residue such as glycine, aminomalonic, benzyl- and p-fluorobenzylamino malonic, or the residue one of a monocarboxylic or bicarboxylic amino acid.

Particularly preferred are compounds of formula (1) wherein R is a residue of L-alanine, L-phenylalanine, L-p-fluoro-phenylalanine, L-methionine or L p-(2'-methoxyphenyl)-phenylalanine.

Preferred amides of formula (1) are those wherein R is H, a —$SO_2$—$CH_3$ group, a polyoxyethylene residue of formula —($CH_2$—$CH_2$—O)$_2$—P wherein P represents H, methyl, ethyl, isopropyl or $CH_2$—$CO_2R_1$ wherein $R_1$ is H or $C_1$–$C_3$ alkyl.

Preferred amides of formula (1) are also those wherein R is a substituent of formula (3)

$(CH_2)_m$-Φ  (3)

wherein, when m is an integer from 2 to 3, Φ is a basic residue selected from the groups N,N-diethyl-amino, 4-morpholyl, 1-piperidyl, 1-(4-benzyl)piperazinyl, 1-(4-diphenylmethyl)-piperazinyl, 1-(4-(4',4''-difluoro-diphenyl)methyl)-piperazinyl, while, when m is zero, Φ is preferably a heteroarylic residue such as 2- or 4-pyridyl, 2 or 4-pyrimidinyl, 2-pyrazinyl, 2-1,3-thiazolyl, 2-1,3-thiazolidinyl, 2-imidazolyl, more preferably 4-pyridyl.

The compounds of the invention as defined in Formula (1) are obtained using well known methods, consisting in the reaction of an activated form of an acid of formula (4):

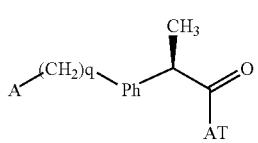

(4)

wherein A and $(CH_2)_q$ are as previously defined and AT is a residue activating the carboxyl group, with an amine of formula (5):

R—$NH_2$  (5)

in non-racemizing conditions, in the presence, if desired, of a molar excess of a base. Examples of activated forms of the acids formula (4 AT=H) are the corresponding chlorides (AT=Cl), imidazolides (AT=1-imidazol), esters with phenols such as p-nitrophenol (AT=$pNO_2$—$C_6H_4O$—) or activated forms obtained by reaction in presence of 1-hydroxybenzotriazole (HOBT) or a carbodiimide (such as cyclohexylcarbodiimide).

In the primary amines of formula (5), R has the meaning as above defined:

The reactions for the preparation the amides of formula (1) are usually carried out at room temperature, by using conventional protic or aprotic solvents, preferably made anhydrous on molecular sieves, or mixtures thereof.

Said solvents comprise esters such as ethyl acetate, methyl acetate, ethyl formate, nitriles such as acetonitrile, straight or cyclic ethers such as dioxan, tetrahydrofuran, ethyl ether, sulfolan, amides such as dimethylformamide, formamide; halogenated solvents such as dichloromethane, aromatic hydrocarbons such as toluene, chlorobenzene and heteroaromatic hydrocarbons such as pyridine and picoline.

The reactions can be carried out in the presence of a base. Preferred inorganic bases are alkaline or alkaline-earth carbonates and bicarbonates such as finely ground potassium carbonate, potassium bicarbonate and Mg and Ca carbonates.

If desired, the compounds of formula (1), can be transformed into other compounds of formula (1) by cleaving any protecting groups and/or by selective hydrolysis of ester groups. A particularly preferred ester group is allyl, cleavable in highly selective conditions, e.g. based on the transfer of the allyl group to a morpholine molecule that, in the presence of Pd(0) as catalyst, acts as H transfer agent and as nucleophile acceptor according to the process described in J. Org. Chem., 54, 751, 1989.

Finally, if desired, a formula (1) compound can be converted into a salt using pharmaceutically acceptable acids or bases.

Examples of pharmaceutically acceptable acids comprise hydrochloric, sulfuric, nitric, phosphoric acid, or mono- or poly-basic organic acids such as acetic, benzoic, tartaric, citric, fumaric, maleic, malic, mandelic, oxalic and malonic acid.

Examples of pharmaceutical acceptable salts are those with the cations of alkaline and alkaline-earth metals preferably sodium and magnesium, and those with organic bases such as tromethamine, D-glucosamine, lysine, arginine, tetraethylamonium. The R-enantiomers of 2-(aminoaryl)propionic acids of formula (4a)

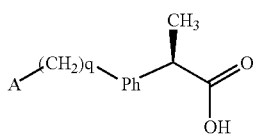

(4a)

are well known compounds that, unlike the corresponding S-enantiomers, are characterized by not being effective inhibitors of cyclooxygenase enzymes.

Among the R-2-aryl-propionic acids of formula (4a) wherein q is zero, the following are particularly preferred: R-2-[4-(2,5-dihydro-1H-pyrrol-1-)-phenyl]-propionic, R-2-[4-(1H-pyrrol-1-)-phenyl]-propionic, R-2-[4-(1H-pyrrolidin-1-yl-)-phenyl]-propionic, R-2-(4-piperidinophenyl)-propionic, R-2-(4-morpholinophenyl)-propionic, R-2-(4-thiamorpholinophenyl)-propionic, R-2-(4-(4'-benzyl-piperazin-1'-yl)-phenyl)-propionic and its 3-chloro derivatives, R-2-(4-(4'-benzhydryl-piperazin-1'-yl)-phenyl)-propionic and its 3-chloro derivative. All these acids are well known compounds and are obtained using well known methods. General guidelines for the synthesis and the optical resolution of the said acids of formula (4a; q=0) are found in U.S. Pat. No. 3,641,040; U.S. Pat. No. 3,993,763; U.S. Pat. No. 3,997,669 and U.S. Pat. No. 4,337,264. More particularly described in these patents are the syntheses of the methyl and ethyl esters of 2-(4-aminophenyl)-propionic acid and the 2-(3-chloro-4-aminophenyl)-propionic derivative which, by reaction with a convenient α,ω-alkane or alkene variously substituted, is transformed into the desired 1-aza-cycloalkane or cycloalkene.

By way of example, in the following scheme of reaction discloses the method of preparation used in the synthesis of esters of 2-(4-piperazin-1-yl-phenyl)-propionic acids of formula (4b):

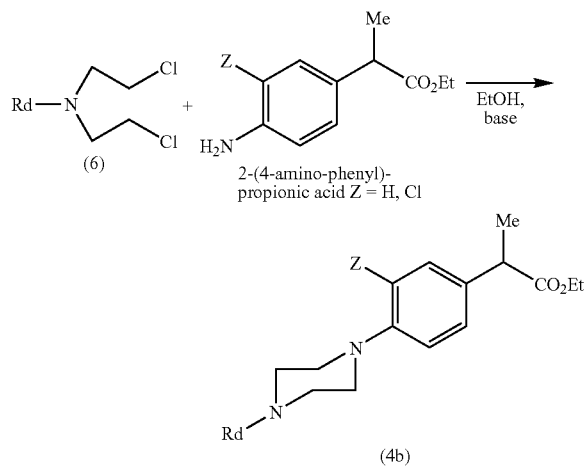

starting from an ester of 2-(4-amino-phenyl)-propionic acid by reaction with a bis-(2-chloroethyl)amine of formula (6) wherein $R_d$ is Boc, $C_1$–$C_3$-alkyl, phenyl, benzyl, benzhydryl, 4,4'-difluoro-benzhydryl.

Among the R 2-aryl-propionic acids of formula (4), wherein q is the integer 1, the following are particularly preferred:

R-2-[4-(2,5-dihydro-1H-pyrrol-1-methyl)phenyl]-propionic, R-2-[4-(1H-pyrrol-1-methyl)phenyl]-propionic, R-2-[4-(1H-pyrrolidin-1-yl-methyl)-phenyl]-propionic, R-2-[4-(1H-pyrrolidin-3-one-1-yl-methyl)-phenyl]-propionic, R-2-[4-(piperidin-1-yl-methyl)-phenyl]-propionic, R-2-(4-piperidin-4-one-1-yl-methyl-phenyl)-propionic, R-2-(4-morpholin-4-yl-methyl-phenyl)-propionic, 4-(thiomorpholin-4-yl-methyl)-phenyl-propionic, R-2-[4-(4'-benzyl-piperazin-1'-yl-methyl)-phenyl)]-propionic, R-2-[4-(4'-benzhydrylpipera-1'-yl-methyl)phenyl]-propionic acids.

Their preparation is based on the conversion of tert-butylester of a 2-tolyl-propionic acid into the corresponding Br-methyl-derivative, which is then transformed into tert-butylester of an acid formula (4a, q=1) by reaction with the desired amine of formula A-H (where A is as already defined).

The allyl and benzyl esters of α- or ω-amino acids are well known commercially available products, or they can be prepared using well known methods; for the preparation of allyl esters see e.g. H. Waldmann and H. Kunz, Liebigs Ann. Chem., 1712, 1983 and J. Org. Chem, 1989 already cited; for the preparation of benzyl esters see e.g. Mac Leod A M et al, J. Med. Chem., 37, 1269, 1994.

For the evaluation of the pharmacological activity certain compounds of the invention of formula (1) were used in in vitro experiments on polymorphonucleated leucocytes (hereinbelow referred to as PMN isolated from heparinized human blood taken from compliant healthy adult subjects, by means of sedimentation on dextran following the procedure described by W. J. Ming et al, J. Immunol., 138, 1469, 1987. Each of the compounds under examination was pre-incubated for 10 mins. at a temperature of 37° C. In the experiments of chemotaxis, in those directed to measure the tyrosine-kinase activity and in those directed to measure the cytosolic $Ca^{2+}$ levels, human recombinant interleukin-8 (rhIL-8, Pepro Tech) was used: the lyophilized protein was dissolved in HBSS (Hanck's balanced salts solution) at a concentration of 100 mcg/ml and then diluted to concentrations of 10 ng/ml in the chemotaxis experiments and to 25–50 ng/ml in the evaluation of the $Ca^{2+}$ (i.e. $[Ca_{2+}]_i$) intracellular modifications and to 400 ng/ml in the evaluation of the tyrosine-kinase activity.

During the chemotaxis test (according to W Falket et al, J. Immunol. Methods, 33, 239, 1980) 5 mcm-pore PVP-free filters and micro-chambers suitable for carrying out replications were used. The compounds were evaluated in the concentration range from $10^{-6}$ to $10^{-10}$ M, using R(–)-2-(4-isobutylphenyl)-propionyl methansulfonamide whose $ED_{50}$ is equal to $10^{-9}$ M as reference standard.

Furthermore, the compounds of the invention were able to inhibit IL-8 induced tyrosine-kinase activity, notoriously critical for PMN chemotaxis (Yasui et al, 1994, already cited). Said evaluation was performed using the method described by L'Heureux et al, Blood, 85, 522, 1995. Finally, some of the compounds of the invention were able to inhibit IL-8 induced increase of intracellular $Ca^{2+}$ ion concentration, said evaluation being performed according to the experimental model described by C. Bizzarri et al, Blood, 86, 2388, 1995.

As previously stated, the compounds according to the invention did not show ability to inhibit CO enzymes when evaluated ex vivo in the blood in toto according to the procedure disclosed by Patrignani et al, in J. Pharmacol. Exper. Ther., 271, 1705, 1994. Moreover, in nearly all cases, the compounds of the invention of formula (1) do not interfere with the production of $PGE_2$ induced in the murine macrophages by stimulation with lipopolysaccharides (LPS. 1 μg/ml) in the concentrations range from $10^{-5}$ to $10^{-7}$ M. Any inhibition of the $PGE_2$ production that can be recorded is mostly at the limit of the statistical significance and most times less than 15–20% of the base value.

This insignificant inhibition of $PGE_2$ synthesis allows compounds of the invention of formula (1) to be clearly differentiated from (S)-enantiomers of 2-arylpropionic acids and from amides thereof which, on the contrary, because of their pronounced inhibition of $PGE_2$ synthesis constitute a stimulus for same murine macrophages to amplify the synthesis of TNF-α.

It is well-known that an amplification of the synthesis TNF-α allows amplification of the activation of neutrophils and favours their chemotaxis besides being a stimulus of IL-8 synthesis. The compounds of the invention of formula (1) do not show any interference with the PG synthesis, while an inhibitory effect is recorded for some of them towards the synthesis of TNF-α which is usually stimulated in macrophages by LPS, an inhibitory effect that is also recorded towards the synthesis of the same cytokine after stimulation with $H_2O_2$.

In consideration of the experimental evidence discussed above and the involvement of IL-8 and its derivatives as the most important mediators and promoters of neutrophil infiltration in pathologies such as psoriasis (R. J: Nicholoff et al, Am. J. Pathol., 138, 129, 1991), the rheumatoid arthritis (M. Selz et al, J. Clin. Invest., 87, 463, 1981), ulcerative colitis (Y. R. Mahla et al, Clin. Sci, 82, 273, 1992) acute respiratory failure and the idiopathic fibrosis (E. J. Miller already cited and P. C. Carré et al, J. Clin. Invest., 88, 1882, 1991), glomerulonephritis (T. Wada et al, J. Exp. Med., 180, 1135, 1994) and in the prevention of the damage from ischemia and reperfusion, the compounds of the invention are thought particularly useful in achieving these therapeutic aims.

For this purpose, the compounds of the invention are conveniently formulated in pharmaceutical compositions using conventional technical and eccipients such as, e.g. those described in "Remington's Pharmaceutical Sciences Handbook" Mack Publishing, New York, 18° Ed., 1990.

The compositions of the invention can be administered intravenously, as a bolus, or orally in the form of capsules, tablets, syrup, and controlled release formulations, as well as in preparations for dermatological use (creams, lotions, spray and ointments). The average daily dosage will depend on several factors such as the severity of the disease and on the conditions of the patient (age, sex and weight). The dose will vary generally from 1 or a few mg to 1500 mg of the compounds of formula (1) per day, optionally in divided multiple administrations. Higher doses can be administered for long periods of time, also thanks to the low toxicity of compounds of the invention.

The following examples illustrate the invention.

In the description of the absolute configuration of the single chiral substituents optionally present in compounds of the invention, apexes (e.g. R', S', S" etc.) will be used as a rule to indicate absolute configurations present in the substituent R linked to the Nitrogen atom of said compounds.

Examples of abbreviations are: THF for tetrahydrofuran, DMF for dimethylformamide, AcOEt for ethyl acetate. HOBT for 1-hydroxybenzotriazole, DCC for diclohexylcarbodiimide.

EXAMPLE 1

R—N-2-[4-(pyrrolidin-1'-yl)methylphenyl]propionyl-methanesulfonamide

N,N-dimethylaminopyridine (2.4 g~0.02 mol), N-(3-dimethylaminopropyl)-N'-ethylcarbodiimide hydrochloride (3.73 g~0.02 mol) and methansulfonamide (1.85 g, 0.02 mol) are added in that order to a solution of 2-[(4-(pyrrolidin-1-il)methylphenyl]propionic acid (4 g, approximately 0.019 mol) in anhydrous $CH_2Cl_2$ (30 ml). The mixture is left under stirring overnight. The solvent is evaporated under vacuum and the residue is taken up with ethyl acetate (3×15 ml). The organic phases are combined, washed with water to neutrality, dried on sodium sulfate and evaporated to dryness. The residue is purified on a silica gel column to give 3.15 g of R—N-2-[4-(pyrrolidin-1'-yl)methylphenyl]propionyl-methanesulfonamide.

EXAMPLE 2

R—N-2-[4-(4'-benzyl-piperazin-1'-yl-aminomethyl)-phenyl]-propionylmethanesulfonamide Methanesulfonamide (2.3 g, 0.0243 mol) is added to a suspension of t-BuOK (2.73 g, 0.0244 mol) in anhydrous THF (30 ml). The mixture is stirred for 30 mins at room temperature then cooled to −25° C., then a precooled solution of imidazolide of R-2-[4-(4'-benzyl-piperazin-1'-yl) aminomethyl-phenyl)]-propionic acid (5.45 g~0.019 mol) in THF (10 ml) is added. Stirring is continued at this temperature for 2 h then for 1 hour at 0° C. The reaction mixture is neutralized by adding 0.04 molar equiv. of a solution of glacial AcOH in THF. After separation by filtration of the inorganic salts that have separated, the solvent is evaporated under vacuum and the oily residue is partitioned between dichlorornethane (30 ml) and a solution of 2.5% $NaHCO_3$. The organic extracts are combined, washed with water, dried on sodium sulfate. After evaporation of the solvent and purification on silica gel column 4.05 g of R—N-2-[4-(4'-benzyl-piperazin-1'-yl-aminomethyl)-phenyl]-propionyl-methanesulfonamide are obtained.

EXAMPLE 3

(R,S')-2-[3'-chloro-4-(thiormorfolin-4-yl)phenyl]-N-(2-carboxyethyl)-propionamide To a solution of R-2-[3-chloro-4-(thiomorpholin-4-yl) phenyl]-propionic acid (6.4 g;~22.1 nmol) in DMF (20 ml) cooled to around T=0° C., 3 g of HOBT (22.2 mmol) are added under stirring. After 15', a mixture of L-alanine methyl ester hydrochlorhyde (3.2 g~22.2 mmol) and triethylamine (3 ml) in DMF (5 ml) is added; finally DCC in subsequent portions for a total of 5 g (24.24 mmol) is added. The mixture is kept under stirring for two hours at T=0° C. and thereafter at room temperature overnight. After elimination by filtration of the dicyclohexylurea precipitate, the filtrate is evaporated to a small volume and partitioned between ethyl acetate and a saturated solution of $NaHCO_3$. The organic phases are combined and exhaustively re-extracted with 2N $H_2SO_4$, the acid extracts are combined, ice is added and 2N NaOH is added until neutrality, then re-extracted with AcOEt (50 ml). The organic phase is washed with a 10% solution of sodium sulfate (20 ml). After drying on $Na_2SO_4$ and evaporation of the solvent at reduced pressure, a residue is obtained that, suspended in hexane (60 ml) and kept under stirring overnight, leads to the separation of a white crystalline precipitate made of (R,S')-2-[3-chloro-4-(thiomorpholin-4-yl)phenyl]-N-(2-methoxycarbonyl-ethyl)-propionamide (4.9 g,~16.84 mmol).

A solution of 2 g (6.87 mmol) of the compound in dioxan (9 ml) is added with an equal volume of 1N NaOH (9 ml) and is kept under stirring at room temperature overnight. After dilution with water and ice (130 ml) it is acidified with 2N $H_2SO_4$ to pH 6–6.5. The aqueous phase is extracted exhaustively with $CH_2Cl_2$ (4×20 ml); the organic extracts are combined, washed with a saturated solution of NaCl (20 ml) and dried on $Na_2SO_4$. After evaporation of the solvent at reduced pressure, the residue, crystallized from ethyl ether (30 ml), yelds (R,S')-2-[3'-chloro-4-(thiomorpholin-4-yl) phenyl]-N-(2-carboxyethyl)-propionamide (1.6 g, 6.52 mmol).

By replacing the L-alanine methyl ester with glycine methylester and L-tryptophan 3,5-dimethylbenzylester with L-4-fluoro-phenylalanine benzyl ester in the procedure described above, the following compounds are obtained:
(R)-2-[(3-chloro-4-(thiomorpholin-4-yl)phenyl]-N-(2-methoxycarbonylmethyl)propionamide;
(R,S')-2-[(3-chloro-4-(thiomorpholin-4-yl)phenyl]-N-[1-(3,5-dimethyl-benzyloxycarbonyl)-ethyl-2-(3-indolyl)]-propionamide;
(R,S')-2-[(3-chloro-4-(thiomorpholin-4-yl)phenyl]-N-[1-(benzyloxycarbonyl)ethyl-2-(4'-fluorophenyl]-propionamide.

EXAMPLE 4

R-2-[3-chloro-4-(3-pyrrolyn-1-yl)-phenyl]propionamide

A solution of R(−)-pirprofene (2 g; 9.69 mmol) in thionyl chloride (4 ml) is heated for 3 hours at reflux temperature; after cooling to room temperature, the solvent is evaporated at reduced pressure, the residue is taken up with dioxan two times in succession and solvents evaporated under high vacuum to eliminate the trace residue of thionyl chloride. A solution in anhydrous acetonitrile (4 ml) of the yellow oily residue of R(−) pirprofenoylchloride hydrochloride (2.16 g; 9.6 mmol) is added dropwise to a solution of 28% $NH_4OH$ (10 ml) cooled to 0–5° C., at such speed that the temperature of the mixture does not exceed +5° C. The mixture is stirred for 1H at room temperature to yeld, after evaporation of the solvents, a residue that is dissolved in AcOEt (6 ml). After cooling a precipitate is separated of R-2-[3-chloro-4-(3-pyrrolin-1-yl)-phenyl]propionamide.

EXAMPLE 5

(R)-2-[3-chloro-4-(2,5-dihydro-1H-pyrrol-1)phenyl]N-(N',N'-dimethyl-aminopropyl)propionamide To a solution of (R)-2-[3-chloro-4-(2,5-dihydro-1H-pyrrol-1-)]phenylpropionic acid (5 g; 20 mmol) in anhydrous $CHCl_3$ (20 ml), cooled to around T=0° C., HOBT (2.7 g; 20 mmol) is added under stirring. After 15', a solution of 3-(dimethylamino)propylamine (2.03 g; 20 mmol) in anhydrous $CHCL_3$ (5 ml) is added dropwise; finally DCC is added in successive portions (4.13 g; 20 mmol). When the additions are finished, the mixture is left under stirring for two hours at T=0° C. and thereafter, at room temperature overnight. After filtration of the dicyclohexylurea precipitated, the filtrate is diluted with dichloromethane (50 ml). The organic phase is washed with water (3×15 ml) and with a saturated solution of NaCl (2×20 ml). After drying over $Na_2SO_4$, evaporation of solvents gives a residue that is taken up into anhydrous acetone (5 ml). HCl gas is bubbled through the solution, the desired product precipitates as hydrochloride salt in the form of a white solid which is isolated by filtration and dried under vacuum at T=40° C. to yield 5.37 g (16 mmol) of (R)-2-[3-chloro-4-(2,5-dihydro-1H-pyrrol-1)phenyl]N-(N',N'-dimethyl-aminopropyl)propionamide hydrochloride.

EXAMPLE 6

(R)-2-[3-chloro-4-(2,5-dihydro-1H-pyrrol-1)phenyl]-N-(bis-carboxymethyl)propionamide To a solution (R)-2-[3-chloro-4-(2,5-dihydro-1H-pyrrol-1-)]phenylpropionic acid (5 g; 20 mmol) in anhydrous $CHCl_3$ (20 ml), cooled to around T=0° C., a solution of HOBT (2.7 g; 20 mmol) is added under stirring. After 15' a solution of diethyl aminomalonate hydrochloride (4.23 g; 20 mmol) and triethylammine (2.78 ml, 20 mmol) in anhydrous $CHCl_3$ (5 ml) is added dropwise; finally DCC in successive portions (4.13 g; 20 mmol) is added. When the additions are finished, the mixture is left under stirring for two hours at T=0° C., and thereafter, at room temperature overnight. After filtration of the dicyclohexylurea precipitated, the filtrate is diluted with dichloromethane (50 ml), the organic phase is washed with water (3×15 ml) and with a saturated solution of NaCl (2×20 ml). After drying on $Na_2SO_4$ and evaporation of the solvents, a residue is obtained that is purified by means of flash chromatography (eluent $CH_2Cl_2$/$CH_3OH$ 95:5) to yeld the diethyl ester intermediate (4.9 g; 12 mmol).

To a solution of the diethyl ester (4.5 g; 11 mmol) in anhydrous $CH_2Cl_2$ (30 ml) cooled to T=−10° C. a solution of 1M $BBr_3$ in $CH_2Cl_2$ (12.36 ml) is added, under stirring and by means of a syringe. The mixture is left at T=−10° C. for 1 hour and thereafter at room temperature for 6 hours, until completion of the reaction. The mixture is then diluted with water (30 ml), the two phases are shaken and separated; the aqueous phase is extracted (2×15 ml) with $CH_2Cl_2$. The organic extracts are combined and extracted with a saturated solution of $NaHCO_3$ (3×15 ml); the basic aqueous phase is then acidified to pH=6-6.5 with a saturated solution of monobasic sodium phosphate and counter-extracted with $CH_2Cl_2$ (3×15 ml). The combined organic extracts are washed with a saturated solution of NaCl, dried on $Na_2SO_4$ and evaporated to give (R)-2-[3-chloro-4-(2,5-dihydro-1H-pyrrol-1)phenyl]N-(bis-carboxymethyl)propionamide as a vitrous solid (1.75 g; 4.95 mmol).

EXAMPLE 7

R(−)-2-[3-chloro-4-(piperidin-1-yl)phenyl]-N-(2"-hydroxyethoxy-ethyl)propionamide A solution of R 2-[3-chloro-4-(piperidin-1-yl)phenyl]-propionylchloride (9.5 mmoli) in anhydrous acetonitrile (10 ml) prepared according to the procedure of Ex. 4, is added dropwise at room temperature to a solution of 2-(2-aminoethoxy)ethanol (0.97 ml; 9.7 mmol) and triethylamine (3 ml) in anhydrous $CH_2Cl_2$ (15 ml). The reaction mixture is stirred overnight at room temperature, then evaporated to dryness. The residue is taken up by a 5% solution of ethyl acetate and a 5% solution of potassium bicarbonate, washed with water and then the organic phase is extracted with 2N sulfuric acid. The acidic aqueous phases are combined, ice is added and the aqueous phases are alkalized to pH 8 and repeatedly re-extracted with AcOEt. These extracts are combined and washed with a 10% sodium sulfate solution. After drying on $Na_2SO_4$ and evaporation of the solvent at reduced pressure, a residue is obtained that is purified by flash chromatography (eluent $CH_2Cl_2$/$CH_3OH$ 98:2) to yield, as a transparent oil, 1.87 g of R(−)-2-[3-chloro-4-(piperidin-1-yl)phenyl]-N-(2"-hydroxyethoxy-ethyl)propionamide.

EXAMPLE 8

By using an amine selected from the group of p-methoxyaniline, (R)-1-methyl-2-(2'-hydroxyethoxy)ethylamine, L-methionine methyl ester, L-2'-methoxy-biphenyl-alanine methyl ester and ethyl 3-oxa-5-amino-pentanoate in the procedure of the previous example,
R-2-[3-chloro-4-(piperidin-1-yl)]-N-(4-methoxy-phenyl)-propionamide;
(R,R')-2-[3-chloro-4-(piperidin-1-yl)]-N-[1'-methyl-2'-(2"-hydroxyethoxy)ethyl]-propionamide;
(R,S')-2-[3-chloro-4-(piperidin-1-yl)]-N-[1-methoxycarbonyl-3-methylthiopropyl]-propionammide;
(R,S')-2-[3-chloro-4-(piperidin-1-yl)]-N-[1-methoxycarbonyl-2-(2'-methoxy-biphenyl)-ethyl)]-propionamide;
R-2-[3-chloro-4-(piperidin-1-yl)]-N-[2-(ethoxycarbonyl-methoxy)-ethyl]-propionamide;
are obtained.

EXAMPLE 9

(R)-2-(4-morpholinophenyl)-N-(4'-pyrimidinyl)-propionammide

To a solution of (R)-2-(4-morpholinophenyl) propionic acid (5 g; 21 3 mmol) in anhydrous ethyl acetate (20 ml) N,N'-carbonyldiimidazole (3.8 g; 23.43 mmol) is added under stirring at room temperature. The mixture is stirred for three hours at room temperature and, without isolating the intermediate imidazolide, a solution of 4-aminopyrimidine (2.23 g; 23.43 mmol) in anhydrous ethyl acetate (10 ml) is added. Stirring at room temperature is continued for 8 hours, then the organic phase is washed with a 5% solution of $NaHO_3$ (3×25 ml). The organic phase is extracted with 2N $H_2SO_4$ (5×10 ml); the acidic aqueous phase is then alkalized to pH=8.5–9 with NaOH and is extracted with ethyl acetate (3×15 ml). The extracts are combined, washed with a saturated solution of NaCl (2×25 ml) and dried on $Na_2SO_4$. After evaporation of the solvent at reduced pressure a crude residue is obtained that is purified by means of flash chromatography to give (R)-2-(4-morpholinophenyl)-N-(4'-pyrimidinyl)propionamide as a pure white solid (5.3 g; 17 mmol).

EXAMPLE 10

R-2-[4-((N-ethyl-N-quinolin-2'-yl-methyl-amino)-methyl)phenyl]-N-(2'-allyloxy-carbonyl-methyl)-propionamide To a solution of R-2-[4-((N-ethyl-N-quinolin-2-yl-methyl-amino)-methyl)phenyl]propionic acid (0.47 g, about 1.2 mmol) in anhydrous ethyl acetate 1.1 molar equivalents of N,N'-carbonyl-diimidazole are added at room temperature and under stirring. After 3 h at room temperature, without isolating the intermediate propionylimidazolide, a solution of 1.1 molar equivalents of glycine allylester in anhydrous AcOEt is added. Stirring is continued for 6 h at room temperature, then the reaction mixture is repeatedly washed with a 5% solution of sodium bicarbonate and water until neutrality. The organic phase is repeatedly extracted with a 2N aqueous solution of $H_2SO_4$ (5×8 ml) and with water. The acid aqueous extracts are combined, alkalized and re-extracted with ethyl acetate. The organic phases are combined and washed until neutrality with a 10% solution of sodium sulfate and dried on anhydrous $Na_2SO_4$. After evaporation of the solvent R-2-[4-((N-ethyl-N-quinolin-2'-yl-methyl-amino)methyl)phenyl)]-N-(2'-allyloxy-carbonyl-methyl)-propionamide is obtained.

EXAMPLE 11

(R)-2-[4-((N-ethyl-N-quinolin-2-yl-methylamino) methyl)phenyl]-N-(4'-pyridyl)-propionamide A solution of (R)-2-[4-((N-ethyl-N-quinolin-2-yl-methylamino)methyl)phenyl propionic acid (4 g; 12 mmol) in thionyl chloride (6.2 ml) is heated for three hours at reflux temperature. After cooling to room temperature, the solvent is evaporated at reduced pressure, the residue is taken up two times in succession with dioxan and solvents evaporated at high vacuum in order to eliminate the trace residues of thionyl chloride. The oily residue thus obtained is dissolved in anhydrous $CH_2Cl_2$ (10 ml).

The solution is added dropwise at room temperature to a solution of 4-aminopyridine (2.25 g; 24 mmol) in methylene chloride in presence of an excess of triethylamine. The mixture is stirred overnight at room temperature, then diluted with $CH_2Cl$ (20 ml). The organic phase is washed with water (2×15 ml) and then with a saturated solution of NaCl (15 ml). After drying on $Na_2SO_4$, and evaporation of solvents, the product is obtained in the form of a white solid (3.07 g; 7.8 mmol).

EXAMPLE 12

By using the procedures described in examples 10 and 11, a R-2-(aminophenyl)-propionic acid of formula (4a) is reacted with an heterocyclic amine selected from the group of 2-amino-pyridine, 4-amino-pyridine, 4-amino-pyrimidine, 2-amino-pyrazine, 2-amino-1,3-thiazol, 2-(pyrid-4-yl)-ethylamine, 2-(imidazol-1-yl)ethylamine and the following amides are obtained R-2-[3-chloro-4-(pyrrolidin-1-yl)-phenyl)]-N-(2'-pyridyl) propionamide;

R-2-[3-chloro-4-(3-pyrrolin-1-yl)-phenyl)]-N-(4'-pyridyl)-propionamide;

R-2-[3-chloro-4-(1H-pyrrol-1-yl)-phenyl]-N-(4'-pyridyl)-propionamide;

R-2-[3-chloro-4-(morpholin-4-yl)-phenyl]-N-(1,3-thiazol-2-yl)-propionamide;

R-2-[4-(morpholin-4-yl-aminomethyl)-phenyl]-N-(pyrazin-2-yl)-propionamide;

R-2-[3-chloro-4-(3'-pyrrolin-1-yl)-phenyl]-N-(4'-pyrimidinyl)-propionamide;

R-2-[4-(pyrrolidin-1-yl-methyl)-phenyl)]-N-(4'-pyridyl)-propionamide;

R-2-[4-(3-pyrrolin-1-yl)-phenyl]-N-(4'-pyridylethyl)-propionamide;

R-2-(4-piperidin-1-yl-phenyl)-N-(1-imidazol-ethyl)-propionamide.

EXAMPLE 13

By reacting a solution of R-2-[3-chloro-4-(4'-benzyl-piperazin-1-yl)-phenyl]-propionylchloride in dioxan with an aqueous solution of N-methylamine under Schotten-Baumann conditions R-2-[3-chloro-4-(4'-benzyl-piperazin-1-yl)-phenyl]-N-methylpropionamide is obtained.

Preparations:

A) A mixture of 1.5 g of ethyl 2-(4-aminophenyl)-propionate, 2.3 g of bis(2-chloroethyl)-benzylamine and N-ethyl-diisopropylamine (5 ml) in 25 ml of absolute ethanol is refluxed for 24 h. The mixture is concentrated under vacuum to dryness, the crude product thus obtained is purified on a silica gel column using $CH_2Cl_2$/MeOH 98:2 as eluent to yield 2.21 g of ethyl 2-[4-(4-benzyl-piperazin-1-yl)-phenyl] propionate.

B) 22 g tert-butyl 2-p-tolyl-propionate is dissolved in 200 ml of $CCl_4$ and the solution is brought to the boiling temperature. After the addition of 0.85 g of 1,1'-azo(biscyclohexanenitrile), 18.7 g of N-bromosuccinimide are added in portions and the reflux temperature is maintained at for 1 h. the mixture is cooled down to 0° C. and filtered from the succinimmide. By concentration of the solution 19.8 g of tert-butyl 2-(4-bromomethyl-phenyl)propionate precipitate.

According to the described methodology and starting from the corresponding tert-butyl 2-o-tolyl-propionate and tert-butyl 2-m-tolyl-propionate, tert-butyl 2-(2-bromomethyl-phenyl)propionate and tert-butyl 2-(3-bromomethyl-phenyl)propionate were prepared.

C) To a solution of 3-pyrroline (2.56 ml; 33.4 mmol) in anhydrous $CH_2Cl_2$ (20 ml) kept at room temperature, a solution of tert-butyl 2-(4-bromomethylphenyl)propionate (5 g; 16.7 mmol) in anhydrous $CH_2Cl_2$ (10 ml) is added, dropwise. When the additions are finished, the solution is brought to reflux and left at said temperature for 12 hours, until completion of the reaction. After cooling to room temperature the mixture is diluted with equal volumes of 5% $NaHO_3$ and $CH_2Cl_2$ (25 ml), shaken and the two phases are separated; the organic phase is further washed with water (2×20 ml) and with a saturated solution of NaCl (2×20 ml). After drying on Na$_2$SO$_4$, evaporation of the solvent yelds pure tert-butyl 2-[4-(2,5-dihydro-1H-pyrrol-1-yl-methyl) phenyl]propionate in the form of pale yellow oil (4.25 g; 15.03 nunol).

The ester (4 g; 14.1 mmol) is dissolved in anhydrous CH$_2$Cl$_2$ (10 ml): The solution is cooled down to T=0° C. and trifluoroacetic acid (14 ml) is slowly added dropwise. When the dripping is finished, the mixture is left under stirring for 6 hours at room temperature. The reaction is blocked by evaporating solvents to dryness and eliminating all solvents present by evaporation with toluene (2×15 ml). The residual oil is kept under stirring in hexane-ethyl ether (1:1, 50 ml) overnight. The precipitate formed is filtered to give 2-[4-(2, 5-dihydro-1H-pyrrol-1-ylmethyl)phenyl]propionic acid as a trifluoroacetate, white solid (1.95 g; 8.6 mmol). The optical resolution of the acid thus obtained was carried out according to the method described in Arzneim. Forsch.-Vol. 46 (II), 9, 891–894, 1996 for the preparation of R-pirprofen.

EXAMPLE 14

(R)-2-[4-(2,5-dihydro-1H-pyrrol-1-ylmethyl)phenyl] propionyl methanesulfonammide The methanesulfonamide is prepared by starting from the optically active acid (R) according Example 2. The final purification of the product is achieved by means of flash chromatography (eluent CH$_2$Cl$_2$/CH$_3$OH 98:2). The pure product is obtained as white solid.

EXAMPLE 15

(R)-2-[4-(2,5-dihydro-1H-pyrrol-1-yl-methyl)phenyl]-N-(2-carboxyethyl)propionamide The amide of the (R) optically active acid with L-alanine was prepared according to Example 3.
The final purification of the product is carried out by crystallization from ethyl ether

EXAMPLE 16

(R)-2-[4-(2,5-dihydro-1H-pyrrol-1-ylmethyl)phenyl] propionamide

The primary amide of the (R) optically active acid was prepared according to Example 4.
The final purification of the product is carried out by crystallization from ethyl acetate.

The invention claimed is:
1. Process for the preparation of an amide of the (R)— enantiomers of 2-arylpropionic acids of formula (1):

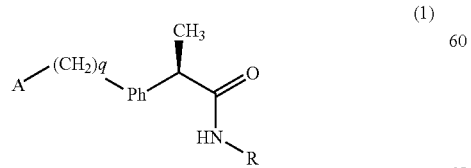

and pharmaceutically acceptable salts thereof, wherein:

q is zero or the integer 1;
Ph represents a phenylene group linked to the group —(CH$_2$)$_q$-A in its position 2, 3 or 4 and optionally substituted in the remaining positions by one or more substituents, same or different, chosen from C$_1$–C$_3$-alkyl, halogens, C$_1$–C$_3$-alkoxy, hydroxy, SH, C$_1$–C$_3$-alkylthio, nitro, haloalkyl,
R is hydrogen, C$_1$–C$_3$-alkyl or the residue of a C$_1$–C$_3$-alkanoic acid, or an amino acid;
A is:
a N—C$_1$–C$_5$-alkylamino group, a N,N— C$_1$–C$_5$-dialkylamino group, a N— C$_1$–C$_8$-alkanoyl(cycloalkanoyl, arylalkanoyl)-N—C$_1$–C$_5$-alkylamino group;
a heterocyclic ring selected from the group consisting of: piperazine, pyrroline, thiomorpholine, morpholine, quinoline and piperidine;
a residue of formula (2a)

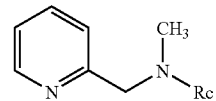

(2a)

wherein R$_c$ is:
—H; —SO$_2$—CH$_3$; C$_1$–C$_3$-alkyl, a residue of formula —CH$_2$—CH$_2$—X—(CH$_2$—CH$_2$O)$_n$—P where P is H, methyl, ethyl, isopropyl; —CH$_2$CO$_2$R$_1$, wherein R$_1$ is H or C$_1$–C$_3$; n is an integer from 0 to 5, X is O or S;
a residue of formula (3)

—(CH$_2$)$_m$-Φ  (3)

wherein, when m is an integer from 2 to 3, Φ represents an unsubstituted or substituted phenylene as defined above, 2-(1-methyl-pyrrolidyl), 2-pyridyl, 4-pyridyl, 1-imidazolyl, 4-imidazolyl, 1-methyl-4-imidazolyl, 1-methyl-5-imidazolyl, or a group —NRa,Rb wherein each of Ra and Rb, same or different, represents C$_1$–C$_5$-alkyl or hydroxyalkyl-(CH$_2$)$_{m_i}$—OH wherein m$_i$ is an integer from 2 to 3; when m is zero, Φ is selected from the group of 2- or 4-pyridyl, 2- or 4-pyrimidinyl, 2-pyrazinyl, 5-methyl-2-pyrazinyl, 1-1,2,4-thiadiazolyl, 3-1,2,4-triazolyl, 3-1-benzyl-1,2,4-triazolyl, 2-1,3-thiazolidinyl, 2-1,3-thiazolyl, 3-isoxazolyl, dihydro-isoxazol-4-yl, 5-methyl-isoxazol-4-yl, 2-imidazolyl, imidazol-4-yl-5-carboxyamide, imidazol-2-yl-4,5-dicarbonitrile, 5-indanyl, 5-indazolyl, 7-aza-indol-3-yl, indol-3-yl, 2- or 3- or 4-quinolyl;
a residue of an α-amino acid selected from the group of alanine, valine, leucine, isoleucine, nor-leucine, phenylalanine, p-fluoro-phenylalanine, tyrosine, biphenylalanine, 2'-methoxy-biphenylalanine, tryptophan, 7-azatryptophan, histidine, S-methylcysteine, carboxy-methylcysteine, methionine, O-methyl-serine, O-ethyl-serine, glycine, phenyl- or p-fluorophenyl-glycine;
a residue of an acid chosen from the group of β-alanine, γ-aminobutyric, δ-aminovaleric, cis-4-amino-cyclohexanecarboxylic, trans-4-amino-methylcyclohexanecarboxylic and 3-amino-1,5-pentadioic acid;

a residue of formula (3a)

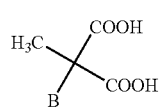

wherein B represents H; a straight or branched $C_1$–$C_5$-alkyl; $(CH_2)_{ni}$—$NH_2$; $(CH_2)_{ni}$—NH-t-butoxycarbonyl; —$(CH_2)_{ni}$—NH-benzyloxycarbonyl; —$(CH_2)_{ni}$—$CO_2H$ wherein $n_i$ is an integer between 1 and 3; benzyl; p-fluorobenzyl; p-phenyl-benzyl; p-(2-methoxy-phenyl)-benzyl; —$CH_2O$—$C_2H_5$; —$CH_2$—S—$CH_3$; —$CH_2$—S—$CH_2$—$CO_2H$; indolyl-3-methyl; 7-aza-indolyl-3-methyl;

provided that when q is zero, R is $SO_2CH_3$ and Ph is 3-chloro-1,4-phenylene, A is other than 1-2,5-dihydropyrrolidino, comprising:

reacting an activated acid derivative of Formula (4)

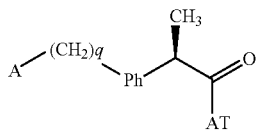

wherein A and q are as defined above and AT is a moiety activating the carbonyl group, with an amine R—$NH_2$, wherein R is hydrogen, $C_1$–$C_3$ alkyl, a halogen, a residue of a $C_1$–$C_3$ alkanoic acid, or an amino acid.

2. A method of inhibiting chemotaxis of neutrophils induced by interleukin-8 in vitro, wherein said method comprises contacting said neutrophils with an effective amount of a compound comprising amides of the (R)—enantiomers of 2-arylpropionic acids of formula (1):

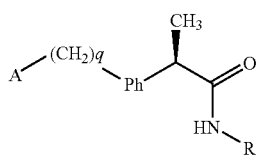

and pharmaceutically acceptable salts thereof, wherein:

q is zero or the integer 1;

Ph represents a phenylene group linked to the group —$(CH_2)_q$-A in its position 2, 3 or 4 and optionally substituted in the remaining positions by one or more substituents, same or different, chosen from $C_1$–$C_3$-alkyl, halogens, $C_1$–$C_3$-alkoxy, hydroxy, SH, $C_1$–$C_3$-alkylthio, nitro, haloalkyl;

A is:
a N—$C_1$–$C_5$-alkylamino group, a N,N— $C_1$–$C_5$-dialkylamino group, a N— $C_1$–$C_8$-alkanoyl(cycloalkanoyl, arylalkanoyl)-N—$C_1$–$C_5$-alkylamino group;

a heterocyclic ring selected from the group consisting of: piperazine, pyrroline, thiomorpholine, morpholine, quinoline and piperidine;

a residue of formula (2a)

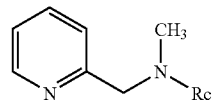

wherein $R_c$, is hydrogen, $C_1$–$C_3$-alkyl or the residue of a $C_1$–$C_3$-alkanoic acid;

R is:
—H; —$SO_2$—$CH_3$; $C_1$–$C_3$-alkyl, a residue of formula —$CH_2$—$CH_2$—X—$(CH_2$—$CH_2O)_n$-P where P is H, methyl, ethyl, isopropyl; —$CH_2CO_2R_1$, wherein $R_1$ is H or $C_1$–$C_3$; n is an integer from 0 to 5, X is O or S;

a residue of formula (3)

—$(CH_2)_m$-Φ  (3)

wherein, when m is an integer from 2 to 3, Φ represents an unsubstituted or substituted phenylene as defined above, 2-(1-methyl-pyrrolidyl), 2-pyridyl, 4-pyridyl, 1-imidazolyl, 4-imidazolyl, 1-methyl-4-imidazolyl, 1-methyl-5-imidazolyl, or a group —$NRa,Rb$ wherein each of Ra and Rb, same or different, represents $C_1$–$C_5$-alkyl or hydroxyalkyl-$(CH_2)_{mi}$—OH wherein $m_i$ is an integer from 2 to 3; when m is zero, Φ is selected from the group of 2- or 4-pyridyl, 2- or 4-pyrimidinyl, 2-pyrazinyl, 5-methyl-2-pyrazinyl, 1-1,2,4-thiadiazolyl, 3-1,2,4-triazolyl, 3-1-benzyl-1,2,4-triazolyl, 2-1,3-thiazolidinyl, 2-1,3-thiazolyl, 3-isoxazolyl, dihydro-isoxazol-4-yl, 5-methylisoxazol-4-yl, 2-imidazolyl, imidazol-4-yl-5-carboxyamide, imidazol-2-yl-4,5-dicarbonitrile, 5-indanyl, 5-indazolyl, 7-aza-indol-3-yl, indol-3-yl, 2- or 3- or 4-quinolyl;

a residue of an α-amino acid selected from the group of alanine, valine, leucine, isoleucine, nor-leucine, phenylalanine, p-fluoro-phenylalanine, tyrosine, biphenylalanine, 2'-methoxy-biphenylalanine, tryptophan, 7-azatryptophan, histidine, S-methylcysteine, carboxy-methylcysteine, methionine, O-methyl-serine, O-ethyl-serine, glycine, phenyl- or p-fluorophenylglycine;

a residue of an acid chosen from the group of β-alanine, γ-aminobutyric, δ-aminovaleric, cis-4-amino-cyclohexanecarboxylic, trans-4-amino-methylcyclohexanecarboxylic and 3-amino-1,5-pentadioic acid;

a residue of formula (3a)

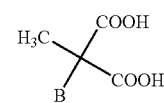

wherein B represents H; a straight or branched $C_1$–$C_5$-alkyl; $(CH_2)_{ni}$—$NH_2$;$(CH_2)_{ni}$—NH-t-butoxycarbonyl; —$(CH_2)_{ni}$—NH-benzyloxycarbonyl; —$(CH_2)_{ni}$—$CO_2H$ wherein $n_i$ is an integer between 1 and 3; benzyl; p-fluorobenzyl; p-phenyl-benzyl; p-(2-methoxy-phenyl)-benzyl; —$CH_2O$—$C_2H_5$; —$CH_2$—S—$CH_3$; —$CH_2$—S—$CH_2$—$CO_2H$; indolyl-3-methyl; 7-aza-indolyl-3-methyl;

provided that when q is zero, R is SO₂CH₃ and Ph is 3-chloro-1,4-phenylene, A is other than 1-2,5-dihydropyrrolidino; and wherein said compound inhibits chemotaxis of neutrophils due to interleukin-8.

3. A method for treating a disease selected from the group consisting of psoriasis, ulcerative colitis, glomerulonephritis, acute respiratory failure, idiopathic fibrosis, rheumatoid arthritis and injury caused by ischemia and reperfusion, comprising administering to a subject presenting said disease an effective amount of a compound comprising an amide of the (R)—enantiomers of 2-arylpropionic acids of formula (1):

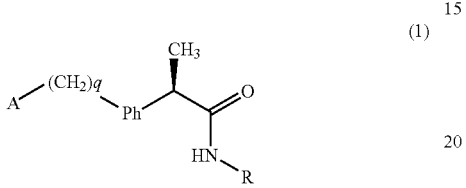

(1)

and pharmaceutically acceptable salts thereof, wherein:
q is zero or the integer 1;
Ph represents a phenylene group linked to the group —(CH₂)$_q$-A in its position 2, 3 or 4 and optionally substituted in the remaining positions by one or more substituents, same or different, chosen from $C_1$–$C_3$-alkyl, halogens, $C_1$–$C_3$-alkoxy, hydroxy, SH, $C_1$–$C_3$-alkylthio, nitro, haloalkyl;
A is:
a N—$C_1$–$C_5$-alkylamino group, a N,N— $C_1$–$C_5$-dialkylamino group, a N— $C_1$–$C_8$-alkanoyl(cycloalkanoyl, arylalkanoyl)-N—$C_1$–$C_5$-alkylamino group;
a heterocyclic ring selected from the group consisting of: piperazine, pyrroline, thiomorpholine, morpholine, quinoline and piperidine;
a residue of formula (2a)

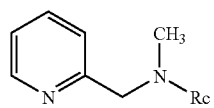

(2a)

wherein $R_c$, is hydrogen, $C_1$–$C_3$-alkyl or the residue of a $C_1$–$C_3$-alkanoic acid;
R is:
—H; —SO₂—CH₃; $C_1$–$C_3$-alkyl, a residue of formula —CH₂—CH₂—X—(CH₂—CH₂O)$_n$—P where P is H, methyl, ethyl, isopropyl; —CH₂CO₂R₁, wherein R₁ is H or $C_1$–$C_3$; n is an integer from 0 to 5, X is O or S;
a residue of formula (3)

—(CH₂)$_m$-Φ   (3)

wherein, when m is an integer from 2 to 3, Φ represents an unsubstituted or substituted phenylene as defined above, 2-(1-methyl-pyrrolidyl), 2-pyridyl, 4-pyridyl, 1-imidazolyl, 4-imidazolyl, 1-methyl-4-imidazolyl, 1-methyl-5-imidazolyl, or a group —NRa,Rb wherein each of Ra and Rb, same or different, represents $C_1$–$C_5$-alkyl or hydroxyalkyl-(CH₂)$_{mi}$—OH wherein $m_i$ is an integer from 2 to 3; when m is zero, Φ is selected from the group of 2- or 4-pyridyl, 2- or 4-pyrimidinyl, 2-pyrazinyl, 5-methyl-2-pyrazinyl, 1-1,2,4-thiadiazolyl, 3-1,2,4-triazolyl, 3-1-benzyl-1,2,4-triazolyl, 2-1,3-thiazolidinyl, 2-1,3-thiazolyl, 3-isoxazolyl, dihydro-isoxazol-4-yl, 5-methyl-isoxazol-4-yl, 2-imidazolyl, imidazol-4-yl-5-carboxyamide, imidazol-2-yl-4,5-dicarbonitrile, 5-indanyl, 5-indazolyl, 7-aza-indol-3-yl, indol-3-yl, 2- or 3- or 4-quinolyl;
a residue of an α-amino acid selected from the group of alanine, valine, leucine, isoleucine, nor-leucine, phenylalanine, p-fluoro-phenylalanine, tyrosine, biphenylalanine, 2'-methoxy-biphenylalanine, tryptophan, 7-azatryptophan, histidine, S-methylcysteine, carboxy-methylcysteine, methionine, O-methyl-serine, O-ethyl-serine, glycine, phenyl- or p-fluorophenyl-glycine;
a residue of an acid chosen from the group of β-alanine, γ-aminobutyric, δ-aminovaleric, cis-4-amino-cyclohexanecarboxylic, trans-4-amino-methylcyclohexanecarboxylic and 3-amino-1,5-pentadioic acid;
a residue of formula (3a)

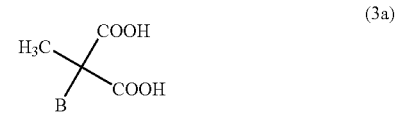

(3a)

wherein B represents H; a straight or branched $C_1$–$C_5$-alkyl; (CH₂)$_{ni}$—NH₂;(CH₂)$_{ni}$—NH-t-butoxycarbonyl; —(CH₂)$_{ni}$—NH-benzyloxycarbonyl; —(CH₂)$_{ni}$—CO₂H wherein $n_i$ is an integer between 1 and 3; benzyl; p-fluorobenzyl; p-phenyl-benzyl; p-(2-methoxy-phenyl)-benzyl; —CH₂O—C₂H₅; —CH₂—S—CH₃; —CH₂—S—CH₂—CO₂H; indolyl-3-methyl; 7-aza-indolyl-3-methyl;
provided that when q is zero, R is SO₂CH₃ and Ph is 3-chloro-1,4-phenylene, A is other than 1-2,5-dihydropyrrolidino; and
wherein said compound inhibits chemotaxis of neutrophils due to interleukin-8.

4. The method according to claim 3 wherein R is a residue of an amino acid selected from the group consisting of glycine, aminomalonic acid, benzyl- and p-fluorobeuzyl-aminomelonic acid, or a residue of a monocarboxylic acid or bicarboxylic α-amino acid.

5. The method according to claim 3 wherein R is a residue of L-alanine, L-phenylalanine, L-p-fluoro-phenylalanine, L-methionine and L-p-(2'-methoxyphenyl)-phenylalanine.

6. The method according to claim 3 wherein R is H, a —SO₂—CH₃ group, a polyoxyethylene residue of formula —(CH₂—CH—O)₂—P wherein P represents H, methyl, ethyl, isopropyl or CH₂—CO₂R₁ wherein R₁ is H or $C_1$–$C_3$ alkyl.

7. The method according to claim 3 wherein R is a substituent of formula (3), and wherein, when m is an integer from 2 to 3, Φ is a basic residue selected from the group of substituents consisting of: N,N-diethyl-amine, 4-morpholyl, 1-piperidyl, 1-(4-benzyl)piperazinyl, 1-(4-diphenylmethyl)-piperazinyl, 1-(4-(4',4"-difluoro-diphenyl)methyl-piperazinyl; or wherein, when m is zero, Φ is an heteroarylic residue such as 2- or 4-pyridyl, 2- or 4-pyrimidinyl, 2-pyrazinyl, 2-1,3-thiazolyl, 2-1,3-thiazolidinyl, 2-imidazolyl and 4-pyridyl.

8. The method according to claim 3 wherein the condition to be treated is psoriasis.

9. The method according to claim 3 wherein the condition to be treated is ulcerative colitis.

10. The method according to claim 3 wherein the condition to be treated is glomerulonephritis.

11. The method according to claim 3 wherein the condition to be treated is acute respiratory failure.

12. The method according to claim 3 wherein the condition to be treated is idiopathic fibrosis.

13. The method according to claim 3 wherein the condition to be treated is rheumatoid arthritis.

14. The method according to claim 3 wherein said chemotaxis of neutrophils follows injury caused by ischaemia and reperfusion.

* * * * *